United States Patent
Boday et al.

(10) Patent No.: US 9,566,548 B2
(45) Date of Patent: Feb. 14, 2017

(54) BUTADIENE SEQUESTRATION VIA SULFUR DIOXIDE CHARGED ZEOLITE BEDS

(71) Applicant: International Business Machines Corporation, Armonk, NY (US)

(72) Inventors: Dylan J. Boday, Tucson, AZ (US); Joseph Kuczynski, North Port, FL (US); Timothy C. Mauldin, San Diego, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 35 days.

(21) Appl. No.: 14/748,742

(22) Filed: Jun. 24, 2015

(65) Prior Publication Data
US 2016/0376207 A1    Dec. 29, 2016

(51) Int. Cl.
| | |
|---|---|
| *B01D 53/44* | (2006.01) |
| *B01D 53/82* | (2006.01) |
| *B01J 19/24* | (2006.01) |
| *C07C 1/32* | (2006.01) |
| *C07D 333/48* | (2006.01) |

(52) U.S. Cl.
CPC ............ *B01D 53/44* (2013.01); *B01D 53/82* (2013.01); *B01J 19/24* (2013.01); *B01J 19/2445* (2013.01); *C07C 1/322* (2013.01); *C07D 333/48* (2013.01); *B01D 2257/7022* (2013.01); *B01J 2219/24* (2013.01)

(58) Field of Classification Search
CPC ...... B01J 19/2445; B01D 53/44; B01D 53/82; B01D 2257/7022; C07C 7/13; C07C 11/167; C07C 1/322
See application file for complete search history.

(56) References Cited

U.S. PATENT DOCUMENTS

| | | | |
|---|---|---|---|
| 2,402,891 A * | 6/1946 | Hooker | C07D 333/48 549/87 |
| 3,446,870 A | 5/1969 | McHarg | |
| 3,992,471 A * | 11/1976 | Priegnitz | C07C 7/13 585/829 |
| 3,998,845 A | 12/1976 | Goldstein et al. | |
| 4,038,156 A | 7/1977 | Knott et al. | |
| 8,044,220 B2 | 10/2011 | Hassan et al. | |

FOREIGN PATENT DOCUMENTS

| | | |
|---|---|---|
| CN | 102336626 A | 2/2012 |
| CN | 102407025 A | 4/2012 |
| CN | 203173942 U | 9/2013 |

(Continued)

OTHER PUBLICATIONS

"Seeking Technology to Neutralize 1,3-Butadiene", Open Innovation, http://documents.specialchem.com/documentsshared/shared/open-innovation/rfps/371/rfp-371-updated.pdf, 2012, 4 pages.

(Continued)

*Primary Examiner* — Lessanework Seifu

(57) ABSTRACT

In an example, a method of butadiene sequestration includes receiving an input stream that includes butadiene. The method includes directing the input stream to a first sulfur dioxide charged zeolite bed for butadiene sequestration via a first chemical reaction of butadiene and sulfur dioxide to form sulfolene.

5 Claims, 8 Drawing Sheets

(56) References Cited

FOREIGN PATENT DOCUMENTS

| CN | 102407025 B | 5/2014 |
|---|---|---|
| CN | 103787811 A | 5/2014 |
| GB | 951501 A | 3/1964 |

OTHER PUBLICATIONS

List of IBM Patents or Patent Applications Treated as Related.
Marcu, et al., "Study of Sulfur Dioxide Adsorption on Y Zeolite", Journal of the Serbian Chemical Society 2004, vol. 69, Issue 7, pp. 563-569.

* cited by examiner

BUTADIENE SEQUESTRATION VIA SULFUR DIOXIDE CHARGED ZEOLITE BEDS

I. FIELD OF THE DISCLOSURE

The present disclosure relates generally to butadiene sequestration via sulfur dioxide charged zeolite beds.

II. BACKGROUND

Butadiene (1,3-butadiene) is produced during combustion and pyrolysis of organic compounds and also through steam cracking of petroleum products. Butadiene is widely used in the production of rubber, plastics and copolymers such as acrylics. Butadiene is indicated to be carcinogenic to humans through inhalation. Approaches to removal of butadiene from a gaseous waste stream (such as via distillation) may be challenging and/or expensive.

III. SUMMARY OF THE DISCLOSURE

According to an embodiment, a method of butadiene sequestration includes receiving an input stream that includes butadiene. The method includes directing the input stream to a first sulfur dioxide charged zeolite bed for butadiene sequestration via a first chemical reaction of butadiene and sulfur dioxide to form sulfolene.

According to another embodiment, a butadiene sequestration system includes a first fluid interface to receive an input stream that includes butadiene. The butadiene sequestration system further includes a first sulfur dioxide charged zeolite bed to sequester butadiene from the input stream via a chemical reaction of butadiene and sulfur dioxide to form sulfolene. The butadiene sequestration system further includes a second fluid interface to provide and output stream from the first sulfur dioxide charged zeolite bed.

According to another embodiment, a method of controlling a butadiene sequestration process is disclosed. The method includes receiving, at a control device, an indication from a butadiene detector that butadiene detected in an output stream exceeds a butadiene threshold. The method further includes sending a first valve positioning signal from the control device to a first valve, the first valve to redirect an input stream that includes butadiene to a sulfur dioxide charged zeolite bed for butadiene sequestration via a chemical reaction of the butadiene and sulfur dioxide to form sulfolene.

One advantage of the present disclosure is the ability to sequester butadiene from a gaseous waste stream via a chemical reaction of butadiene and sulfur dioxide at a sulfur dioxide charged zeolite bed to form sulfolene. Another advantage of the present disclosure is the ability to recharge the zeolite bed with recycled sulfur dioxide that may be produced from the solid sulfolene that is scrubbed from the zeolite bed.

Features and other benefits that characterize embodiments are set forth in the claims annexed hereto and forming a further part hereof. However, for a better understanding of the embodiments, and of the advantages and objectives attained through their use, reference should be made to the Drawings and to the accompanying descriptive matter.

IV. BRIEF DESCRIPTION OF THE DRAWINGS

V. DETAILED DESCRIPTION

The present disclosure relates to systems and methods of butadiene sequestration using one or more sulfur dioxide charged zeolite beds. A sulfur dioxide charged zeolite bed may be used for butadiene sequestration via a chemical reaction of butadiene with sulfur dioxide to form sulfolene. Further, a butadiene detector may be used to monitor an output stream, and when butadiene that is detected in the output stream exceeds a butadiene threshold, a control device (e.g., a programmable logic controller (PLC) device or other computing device) may redirect a butadiene-containing input stream to a second sulfur dioxide charged zeolite bed for butadiene sequestration. While the second sulfur dioxide charged zeolite bed is being used for butadiene sequestration, the first sulfur dioxide charged zeolite bed may be scrubbed to remove the sulfolene and recharged with sulfur dioxide. After being scrubbed and recharged, the first sulfur dioxide zeolite bed may be utilized for butadiene sequestration (e.g., after detection of butadiene in an output stream of the second sulfur dioxide charged zeolite bed).

Figure 2:
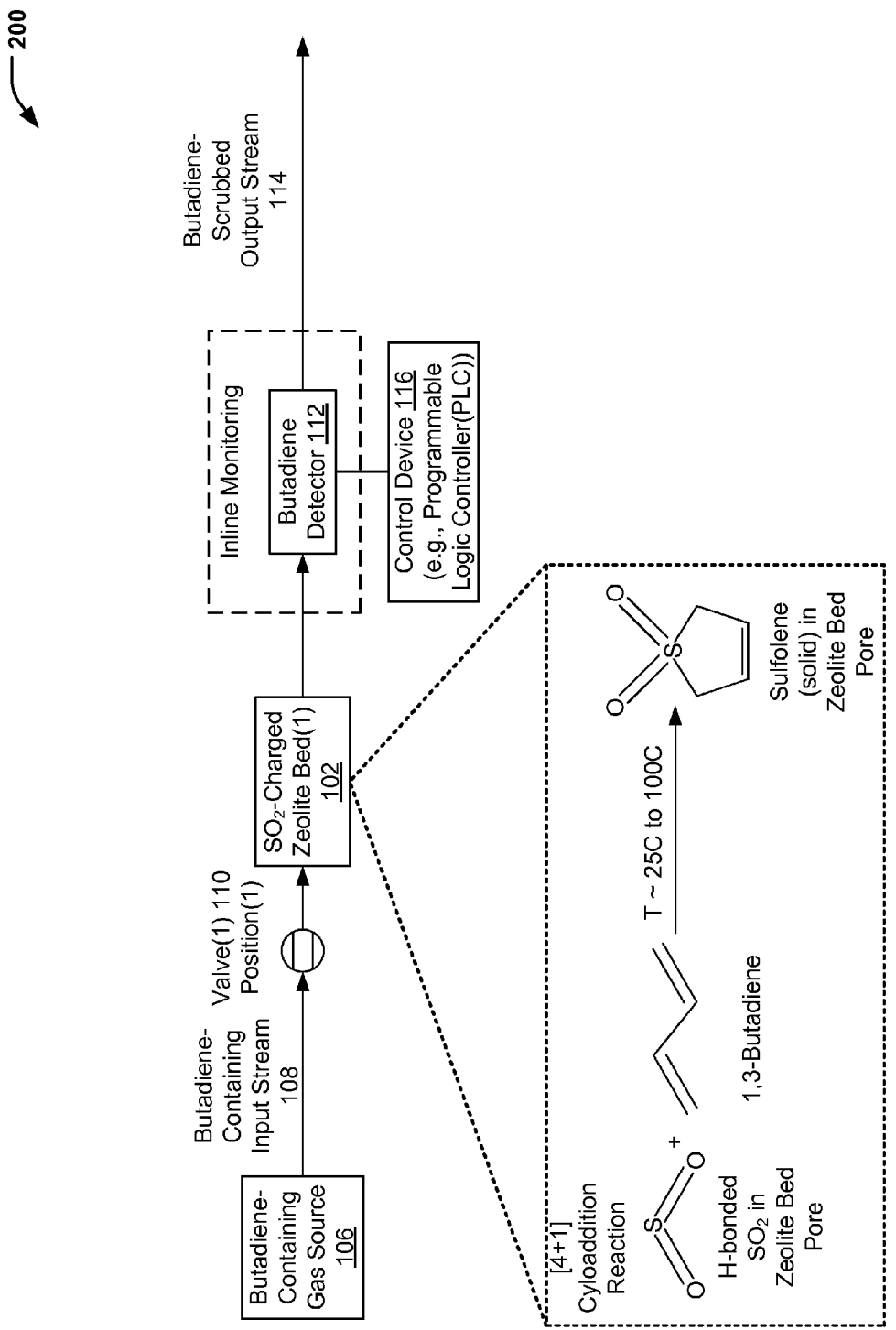
FIG. 2 is a block diagram illustrating an example of butadiene sequestration at a first sulfur dioxide charged zeolite bed via a chemical reaction of sulfur dioxide and butadiene to form sulfolene, according to a particular embodiment.
Figure 3:
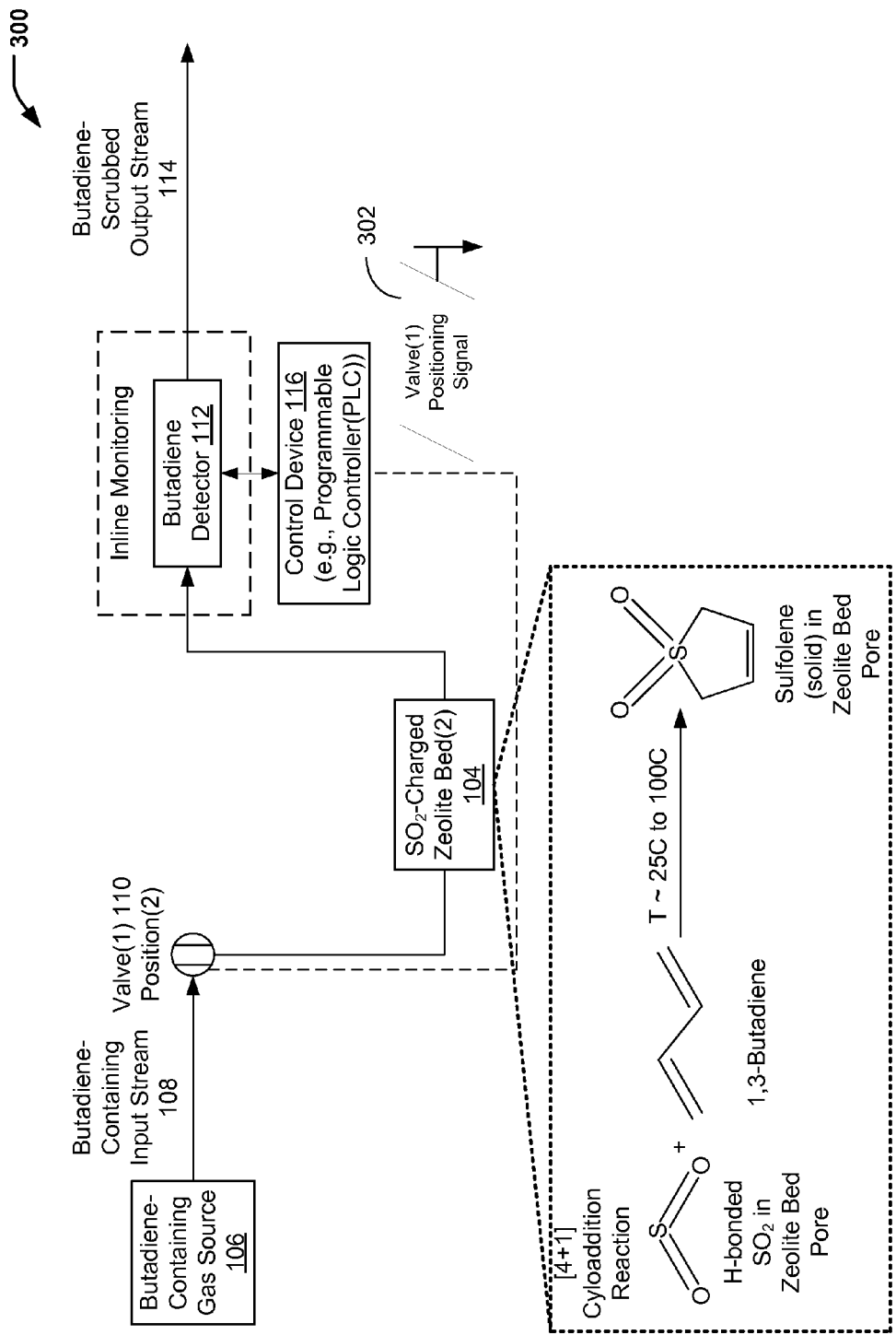
FIG. 3 is a block diagram illustrating an example of butadiene sequestration at a second sulfur dioxide charged zeolite bed (e.g., during recharging of the first zeolite bed of FIG. 2), according to a particular embodiment.

Butadiene (1,3-butadiene) may undergo a cheletropic, [4+1] cycloaddition with sulfur dioxide to form sulfolene (as shown in the chemical reaction diagrams illustrated in FIGS. 2 and 3). Sulfolene may be used as a precursor to industrial solvents or as a safer alternative for transporting butadiene. Reaction between sulfur dioxide and butadiene does not require solvents or additional reagents, and the cycloaddition reaction may occur at room temperature (and accelerates at higher temperatures). Such sulfur dioxide reactivity is specific to butadiene, and therefore competitive reactivity with other waste stream materials may be unlikely. Furthermore, sulfolene is a relatively inert solid. Accordingly, in-situ generated sulfolene may not be a component of a gaseous waste stream. Thus, the present disclosure describes systems and methods of introducing sulfur dioxide (e.g., via hydrogen bonding of $SO_2$ to pores of a zeolite bed) into a gaseous waste stream in order to sequester butadiene in the form of (solid) sulfolene (e.g., in the pores of the zeolite bed).

Figure 1:
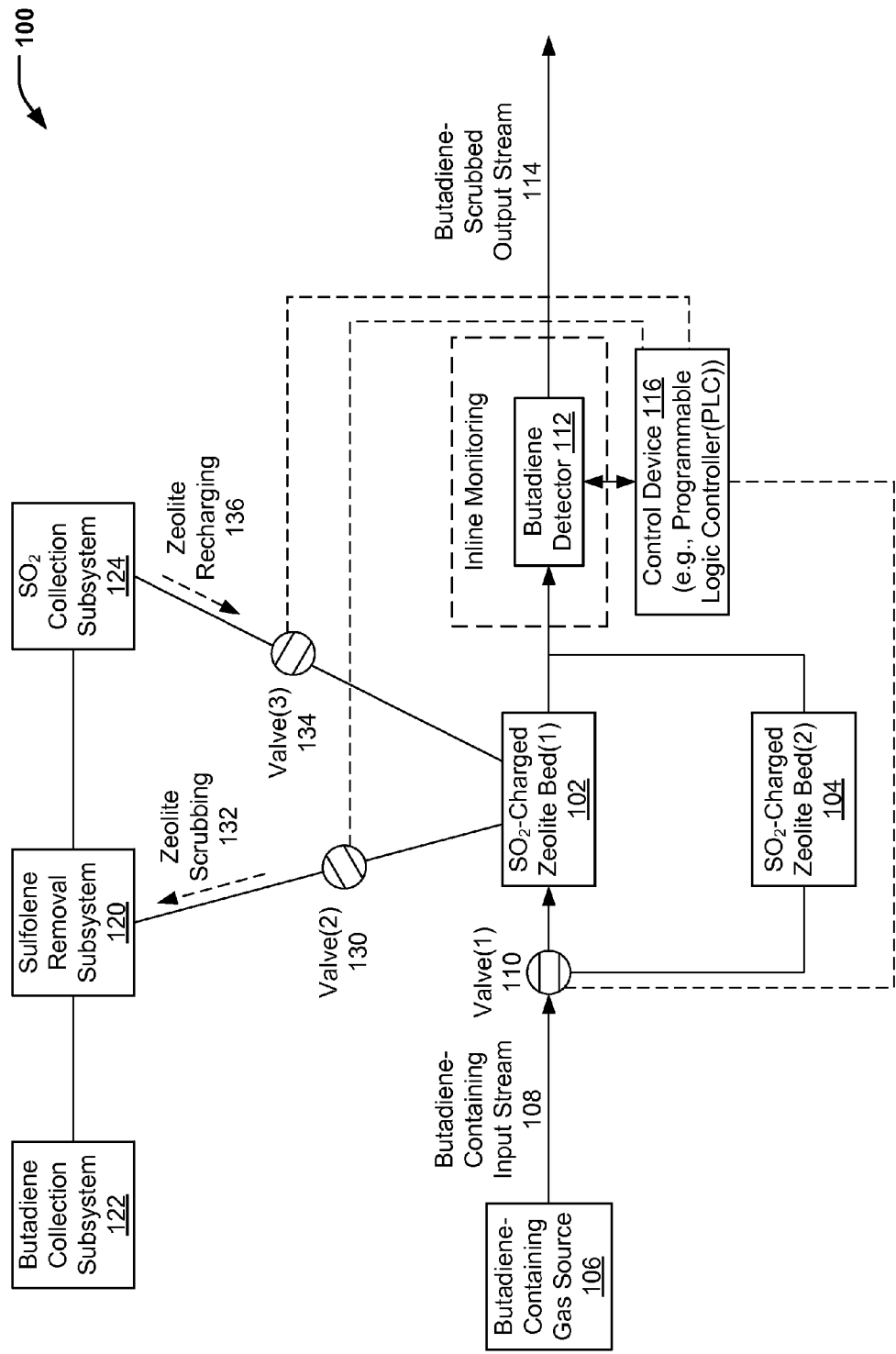
FIG. 1 is a block diagram illustrating an example of a system that utilizes sulfur dioxide charged zeolite bed(s) to sequester butadiene from an input stream by chemically reacting butadiene and sulfur dioxide to form sulfolene, according to a particular embodiment.

Referring to FIG. 1, a block diagram of a particular embodiment of a butadiene sequestration system using sulfur dioxide charged zeolite bed(s) is illustrated and is generally designated 100. In FIG. 1, an input stream (e.g., a gaseous waste stream) that includes butadiene may be directed to a sulfur dioxide charged zeolite bed (or multiple $SO_2$-charged zeolite beds) for butadiene sequestration via a chemical reaction of butadiene and sulfur dioxide to form sulfolene. As illustrated and further described herein with respect to FIG. 2, the chemical reaction includes the butadiene undergoing a cheletropic, [4+1] cycloaddition with the sulfur dioxide to form the sulfolene. As described further herein with respect to FIGS. 3-5, utilizing multiple sulfur dioxide charged zeolite beds allows for sulfolene scrubbing and sulfur dioxide recharging without interrupting a process of sequestering butadiene from the input stream.

In the particular embodiment illustrated in FIG. 1, the butadiene sequestration system 100 includes a first $SO_2$-charged zeolite bed 102 and a second $SO_2$-charged zeolite bed 104. In alternative embodiments, an alternative number and/or arrangement of $SO_2$-charged zeolite beds may be utilized for butadiene sequestration. In the example of FIG. 1, a butadiene-containing gas source 106 provides an input stream 108 that includes butadiene. It will be appreciated that the $SO_2$-charged zeolite beds 102, 104 may be utilized to sequester butadiene from an alternative number of butadiene-containing gas sources and/or input streams containing butadiene.

The butadiene sequestration system 100 includes a first fluid interface (e.g., a first valve 110) to receive the input stream 108 that includes butadiene. In the particular embodiment illustrated in FIG. 1, the first valve 110 is shown in a first operating position to provide a first fluid path to the first $SO_2$-charged zeolite bed 102. As illustrated and further described herein with respect to FIG. 2, the first valve 110 may be configured to provide the first fluid path to the first $SO_2$-charged zeolite bed 102 in the first operating position and to provide a second fluid path (e.g., to the second $SO_2$-charged zeolite bed 104) in a second operating position. As illustrated and further described herein with respect to FIGS. 3-5, when the first valve 110 is in the second operating position, the first $SO_2$-charged zeolite bed 102 may be isolated from the input stream 108 to allow for removal of sulfolene and recharging with sulfur dioxide.

The butadiene sequestration system 100 also includes a butadiene detector 112 for inline monitoring of an output stream 114 (or multiple output streams) of an $SO_2$-charged zeolite bed (or multiple $SO_2$-charged zeolite beds). The butadiene detector 112 is configured to detect and/or quantify butadiene (e.g., an amount, a concentration, etc.) in the output stream 114 (identified as "Butadiene-Scrubbed Output Stream" in FIG. 1). The butadiene sequestration system 100 further includes a control device 116 (e.g., a PLC device) that is communicatively coupled to the butadiene detector 112. The control device 116 may be configured to receive information regarding an amount or concentration of butadiene in the output stream 114 for comparison to a butadiene threshold. The butadiene threshold may represent a particular amount or concentration of butadiene that is indicative of saturation or near saturation of the first $SO_2$-charged zeolite bed 102 with sulfolene or another indication of inadequate sulfur dioxide being available for chemical reaction with butadiene. The control device 116 may be configured to direct the input stream 108 to an alternate $SO_2$-charged zeolite bed for butadiene sequestration in response to determining that butadiene detected in the output stream 114 of a particular $SO_2$-charged zeolite bed exceeds the butadiene threshold. As an example, when the output stream 114 corresponds to an output stream of the first $SO_2$-charged zeolite bed 102, the control device 116 may be configured to direct the input stream 108 to the second $SO_2$-charged zeolite bed 104. As another example, when the output stream 114 corresponds to an output stream of the second $SO_2$-charged zeolite bed 104, the control device 114 may be configured to direct the input stream 108 to the first $SO_2$-charged zeolite bed 104.

In the particular embodiment illustrated in FIG. 1, the butadiene sequestration system 110 further includes a sulfolene removal subsystem 120, a butadiene collection subsystem 122, and a sulfur dioxide collection subsystem 124. As illustrated in the chemical reaction diagram of FIG. 4, in some cases, removal of solid sulfolene from the first $SO_2$-charged zeolite bed 102 may include thermal scrubbing to decompose the sulfolene into butadiene and sulfur dioxide. In this case, butadiene may be separated from the sulfur dioxide and sent to the butadiene collection subsystem 122, and sulfur dioxide may be sent to the sulfur dioxide collection subsystem 124. As illustrated and further described herein with respect to FIG. 5, the sulfur dioxide collected at the sulfur dioxide collection subsystem 124 may be recycled for use in recharging a zeolite bed.

FIG. 1 illustrates that the butadiene sequestration system 100 may include a second fluid interface (e.g., a second valve 130) for removal of the solid sulfolene that is formed in the pores of the first $SO_2$-charged zeolite bed 102 (e.g., during zeolite scrubbing 132). The butadiene sequestration system 100 may also include a third fluid interface (e.g., a third valve 134) for providing additional sulfur dioxide to the first $SO_2$-charged zeolite bed 102 (e.g., during zeolite recharging 136). In the particular embodiment illustrated in FIG. 1, the second valve 130 is shown in a first operating position (e.g., a closed position when not performing the zeolite scrubbing 132), and the third valve 134 is shown in a first operating position (e.g., a closed position when not performing the zeolite recharging 136). As illustrated and further described herein with respect to FIG. 4, the second valve 130 may be configured to provide a path from the first $SO_2$-charged zeolite bed 102 to the sulfolene removal subsystem 120 in a second operating position (e.g., an open position for removal of solid sulfolene via thermal/solvent processing). As illustrated and further described herein with respect to FIG. 5, the third valve 134 may be configured to provide a path from the sulfur dioxide collection subsystem 124 to the first $SO_2$-charged zeolite bed 102 in a second operating position (e.g., an open position for recharging with sulfur dioxide).

In operation, the input stream 108 that includes butadiene is directed to the first $SO_2$-charged zeolite bed 102 via the first valve 110 for butadiene sequestration (when the first valve 110 is in the first position). As illustrated and further described herein with respect to FIG. 2, at least a portion of the butadiene molecules in the input stream 108 react with sulfur dioxide molecules at a plurality of pore locations of the first $SO_2$-charged zeolite bed 102. The butadiene detector 112 monitors the (butadiene-scrubbed) output stream 114 for butadiene. In response to the butadiene detector 112 detecting butadiene in the output stream 114 that exceeds a butadiene threshold, the control device 116 sends a valve positioning signal to the first valve 110 to direct the input stream 108 to the second $SO_2$-charged zeolite bed 104 for butadiene sequestration (as illustrated and further described herein with respect to FIG. 3). As illustrated and further described herein with respect to FIGS. 4 and 5, the control device 116 may send valve positioning signals to the second valve 130 and to the third valve 134 in order to provide fluid paths to the first $SO_2$-charged zeolite bed 102 for performing operations associated with the zeolite scrubbing 132 and the zeolite recharging 136.

Figure 4:
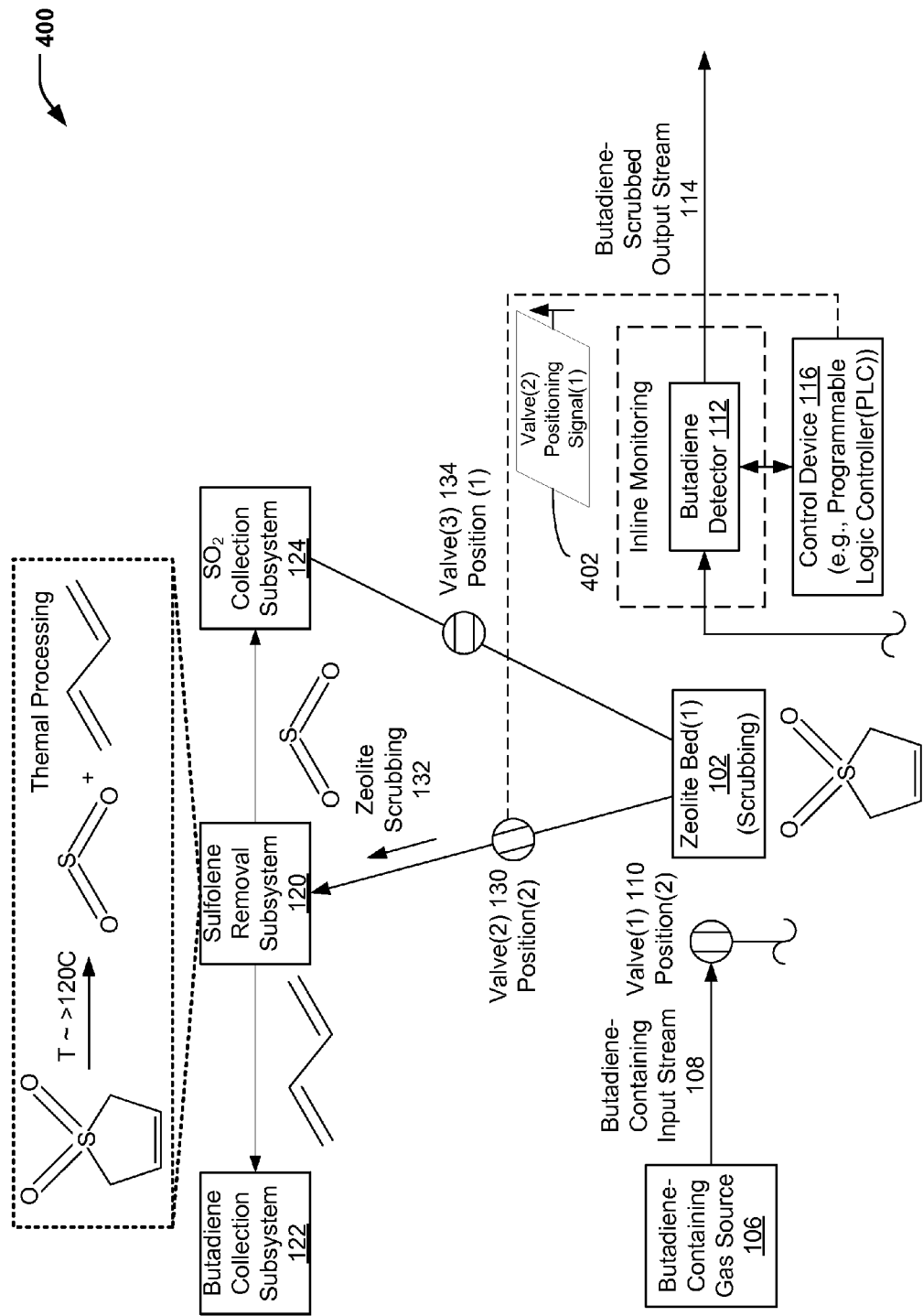
FIG. 4 is a block diagram illustrating an example of zeolite bed scrubbing to remove sulfolene that is formed as a result of the chemical reaction of butadiene and sulfur dioxide, according to a particular embodiment.
Figure 5:
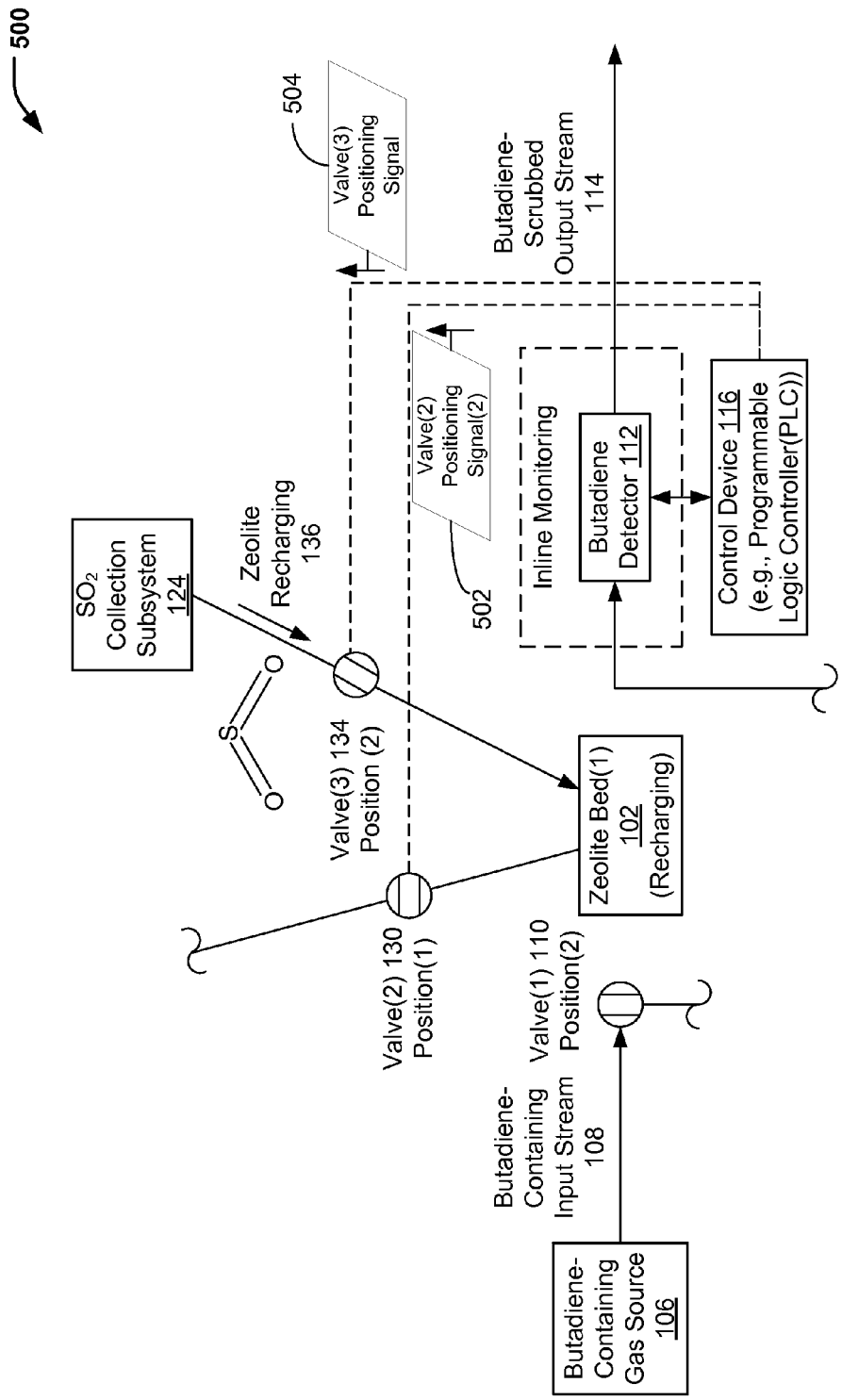
FIG. 5 is a block diagram illustrating an example of zeolite bed recharging with sulfur dioxide after zeolite bed scrubbing to remove the sulfolene from the zeolite bed, according to a particular embodiment.

When the first valve 110 is in the second position, the input stream 108 that includes butadiene is directed to the second $SO_2$-charged zeolite bed 104 for butadiene sequestration. As illustrated and further described herein with respect to FIG. 3, at least a portion of the butadiene molecules in the input stream 108 react with sulfur dioxide molecules at a plurality of pore locations of the second $SO_2$-charged zeolite bed 104. The butadiene detector 112 monitors the (butadiene-scrubbed) output stream 114 for butadiene. In response to the butadiene detector 112 detecting butadiene in the output stream 114 that exceeds a butadiene threshold, the control device 116 sends a valve positioning signal to the first valve 110 to direct the input stream 108 to the first $SO_2$-charged zeolite bed 102 (or to another $SO_2$-charged zeolite bed, not shown in FIG. 1) for butadiene sequestration. While FIGS. 1, 4, and 5 illustrate the second valve 130 and the third valve 134 providing paths to the first $SO_2$-charged zeolite bed 102, it will be appreciated that alternative and/or additional valves may be used to provide fluid paths to the second $SO_2$-charged zeolite bed 104 (for scrubbing/recharging of the second $SO_2$-charged zeolite bed 104).

Thus, FIG. 1 illustrates a butadiene sequestration system that directs a butadiene-containing input stream (e.g., a gaseous waste stream) to one or more $SO_2$-charged zeolite beds for butadiene sequestration via a chemical reaction of butadiene and sulfur dioxide to form sulfolene. FIG. 1 further illustrates that utilizing multiple $SO_2$-charged zeolite beds may prevent interruption of the butadiene sequestration process by redirecting the butadiene-containing input stream from a first $SO_2$-charged zeolite bed to a second $SO_2$-charged zeolite bed in order to allow for sulfolene removal and sulfur dioxide recharging at the first $SO_2$-charged zeolite bed.

FIG. 2 is a diagram 200 illustrating an example of butadiene sequestration at a first sulfur dioxide charged zeolite bed via a chemical reaction of sulfur dioxide (that is hydrogen-bonded in a zeolite pore) and butadiene to form sulfolene. In FIG. 2, selected portions of the butadiene sequestration system 100 of FIG. 1 are shown for illustrative purposes only. In particular, FIG. 2 is designed to illustrate butadiene sequestration via a single $SO_2$-charged zeolite bed (e.g., the first $SO_2$-charged zeolite bed 102). FIG. 3 illustrates selected portions of the butadiene sequestration system 100 of FIG. 1 related to butadiene sequestration via an alternate $SO_2$-charged zeolite bed (e.g., the second $SO_2$-charged zeolite bed 104). FIGS. 4 and 5 illustrate selected portions of the butadiene sequestration system 100 of FIG. 1 related to scrubbing/recharging of a single $SO_2$-charged zeolite bed (e.g., the first $SO_2$-charged zeolite bed 102).

In the particular embodiment illustrated in FIG. 2, the first valve 110 is in a first operating position (identified as "Position (1)" in FIG. 2) to provide a first fluid path for the input stream 108 to the first $SO_2$-charged zeolite bed 102. FIG. 2 includes a chemical reaction diagram illustrating butadiene (1,3-butadiene) undergoing a cheletropic, [4+1] cycloaddition with sulfur dioxide to form sulfolene at the first $SO_2$-charged zeolite bed 102. While FIG. 2 illustrates a single $SO_2$ molecule chemically reacting with a single 1,3 butadiene molecule to form a single sulfolene molecule, it will be appreciated that the first $SO_2$-charged zeolite bed 102 includes multiple sulfur dioxide molecules at multiple zeolite bed pore locations available for chemical reaction with multiple butadiene molecules. FIG. 2 illustrates a particular example of reaction conditions (e.g., a temperature in a range of about 25° C. to about 100° C.), it will be appreciated that the particular reaction conditions may vary. The chemical reaction of sulfur dioxide and butadiene is an equilibrium reaction, with the equilibrium shifted toward sulfolene at temperatures less than about 100° C. As illustrated and further described herein with respect to FIG. 4, the equilibrium may be shifted toward sulfur dioxide and butadiene at temperatures greater than about 100° C. (e.g., greater than about 120° C.).

In FIG. 2, the (butadiene-scrubbed) output stream 114 corresponds to an output stream from the first $SO_2$-charged zeolite bed 102. In this case, the butadiene detector 112 monitors the output stream 114 for butadiene to determine whether detected butadiene exceeds a threshold that may indicate that inadequate sulfur dioxide is available at the first $SO_2$-charged zeolite bed 102 for reaction with butadiene in the input stream 108. As further described herein with respect to FIG. 3, when the detected butadiene exceeds the butadiene threshold, the control device 116 may send a valve positioning signal to the first valve 110 to redirect the input stream 108 to another $SO_2$-charged zeolite bed (e.g., the second $SO_2$-charged zeolite bed 104) for butadiene sequestration. Alternatively (e.g., in cases where alternative $SO_2$-charged beds may not be available for butadiene sequestration), the control device 116 may send a valve positioning signal to close the first valve 110 (e.g., to allow for sulfur dioxide recharging).

Thus, FIG. 2 illustrates an example of butadiene sequestration at a sulfur dioxide charged zeolite bed via a chemical reaction of butadiene included in an input stream (e.g., a gaseous waste stream) and sulfur dioxide to form sulfolene. FIG. 2 further illustrates that inline monitoring of an output stream of the sulfur dioxide charged zeolite bed for butadiene may prevent interruption of the butadiene sequestration process. When butadiene detected in the output stream exceeds a butadiene threshold, the input stream may be directed to an alternate sulfur dioxide charged zeolite bed, as illustrated and further described herein with respect to FIG. 3.

FIG. 3 is a diagram 300 illustrating an example of butadiene sequestration at a second sulfur dioxide charged zeolite bed (e.g., during scrubbing/recharging of the zeolite bed of FIG. 2). In FIG. 3, selected portions of the butadiene sequestration system 100 of FIG. 1 are shown for illustrative purposes only. In particular, FIG. 3 illustrates butadiene sequestration via an alternate $SO_2$-charged zeolite bed (e.g., the second $SO_2$-charged zeolite bed 104).

In the particular embodiment illustrated in FIG. 3, the first valve 110 is in a second operating position (identified as "Position (2)" in FIG. 3) to provide a second fluid path for the input stream 108 to the second $SO_2$-charged zeolite bed 104 for butadiene sequestration via a chemical reaction of sulfur dioxide and butadiene to form sulfolene. FIG. 3 illustrates that the control device 116 may send a valve positioning signal 302 to the first valve 110, and the first valve 110 may change from the first operating position (as shown in FIG. 2) to the second operating position to direct the input stream 108 to the second $SO_2$-charged zeolite bed 104. For example, the control device 116 may send the valve positioning signal 302 to the first valve 110 in response to determining that butadiene detected in the output stream 114 of the first $SO_2$-charged zeolite bed 102 (shown in FIG. 2) exceeds the butadiene threshold.

In FIG. 3, after the first valve 110 is switched to the second operating position to direct the input stream 108 to the second $SO_2$-charged zeolite bed 104, the (butadiene-scrubbed) output stream 114 corresponds to an output stream from the second $SO_2$-charged zeolite bed 104. In this case, the butadiene detector 112 monitors the output stream 114 for butadiene to determine whether detected butadiene exceeds a threshold that may indicate that inadequate sulfur dioxide is available at the second $SO_2$-charged zeolite bed 104 for reaction with butadiene in the input stream 108. While not shown in FIG. 3, when the detected butadiene exceeds the butadiene threshold, the control device 116 may send a second valve positioning signal to the first valve 110 to direct the input stream 108 to another $SO_2$-charged zeolite bed (e.g., the first $SO_2$-charged zeolite bed 102) for butadiene sequestration. For example, the input stream 108 may be directed to the first $SO_2$-charged zeolite bed 102 after scrubbing/recharging of the first $SO_2$-charged zeolite bed 102, as described further herein with respect to FIGS. 4 and 5.

Thus, FIG. 3 illustrates an example of butadiene sequestration at an alternate sulfur dioxide charged zeolite bed via a chemical reaction of butadiene and sulfur dioxide to form sulfolene. As illustrated and further described herein with respect to FIGS. 4 and 5, the alternate sulfur dioxide charged zeolite bed may allow butadiene sequestration to continue during sulfolene scrubbing and sulfur dioxide recharging of another (offline) zeolite bed.

FIG. 4 is a diagram 400 illustrating an example of zeolite bed scrubbing to remove sulfolene that is formed as a result of the chemical reaction of butadiene and sulfur dioxide. In FIG. 4, selected portions of the butadiene sequestration system 100 of FIG. 1 are shown for illustrative purposes only. In particular, FIG. 4 is designed to illustrate scrubbing of a single zeolite bed (e.g., the first $SO_2$-charged zeolite bed 102) to remove solid sulfolene that is formed as a result of the chemical reaction of sulfur dioxide and butadiene.

In the particular embodiment illustrated in FIG. 4, the first valve 110 is in the second operating position to direct the input stream 108 to the second $SO_2$-charged zeolite bed 104 (not shown in FIG. 4) for butadiene sequestration. FIG. 4 illustrates that the control device 116 may send a valve positioning signal 402 to the second valve 130 to open a second (fluid) path to allow for removal of sulfolene from the first $SO_2$-charged zeolite bed 102. For example, the control device 116 may send the valve positioning signal 402 to the second valve 130 after sending the valve positioning signal 302 to the first valve 110 (as shown in FIG. 3). Thus, the second $SO_2$-charged zeolite bed 104 may be used for butadiene sequestration while the first $SO_2$-charged zeolite bed 102 is isolated in order to allow a first set of operations associated with sulfolene removal to be performed.

In some cases, the first set of operations associated with sulfolene removal includes utilizing one or more solvents to remove the sulfolene from the first $SO_2$-charged zeolite bed 102. In other cases, the first set of operations may include thermal processing to remove the sulfolene from the first $SO_2$-charged zeolite bed 102. FIG. 4 includes a chemical reaction diagram of a second chemical reaction to form sulfur dioxide and butadiene from the sulfolene. As previously described with respect to FIG. 2, the chemical reaction of sulfur dioxide and butadiene is an equilibrium reaction, with the equilibrium shifted toward sulfolene at temperatures less than about 100° C. FIG. 4 illustrates that the equilibrium may be shifted toward sulfur dioxide and butadiene at temperatures greater than about 100° C. (e.g., greater than about 120° C.).

In the example of FIG. 4, the thermal processing is illustrated at the sulfolene removal subsystem 120. In some cases, one or more solvents may be used to remove the solid sulfolene from the first $SO_2$-charged zeolite bed 102. In other cases, sulfolene removal from the first $SO_2$-charged zeolite bed 102 may include direct application of heat to the first $SO_2$-charged zeolite bed 102 (e.g., heating to a temperature that is greater than about 120° C.) to decompose the solid sulfolene into gaseous sulfur dioxide and butadiene. In this example, the gaseous sulfur dioxide and butadiene may flow through the second valve 130, and the sulfolene removal subsystem 120 may have a reduced temperature (e.g., less than about 100° C.) where the gaseous sulfur dioxide and butadiene may undergo a second cycloaddition reaction to form solid sulfolene for collection and/or processing.

In the particular embodiment illustrated in FIG. 4, the gaseous sulfur dioxide and butadiene that are formed as a result of the thermal processing of sulfolene may be separated (e.g., via distillation or other separation methods, at the sulfolene removal subsystem 120), with the $SO_2$ sent to the $SO_2$ collection subsystem 124 and the butadiene sent to the butadiene collection subsystem 122. As further described herein with respect to FIG. 5, the sulfur dioxide that is sent to the $SO_2$ collection subsystem 124 may be utilized for zeolite bed recharging.

Thus, FIG. 4 illustrates an example of sulfolene scrubbing/removal from a zeolite bed in order to allow the zeolite bed to be recharged with sulfur dioxide for subsequent butadiene sequestration. FIG. 4 further illustrates that thermal processing of sulfolene may allow sulfur dioxide to be recycled during zeolite bed recharging, as illustrated and further described herein with respect to FIG. 5.

FIG. 5 is a diagram 500 illustrating an example of zeolite bed recharging with sulfur dioxide after zeolite bed scrubbing to remove the sulfolene from the zeolite bed. In FIG. 5, selected portions of the butadiene sequestration system 100 of FIG. 1 are shown for illustrative purposes only. In particular, FIG. 5 illustrates recharging of a single zeolite bed (e.g., the first $SO_2$-charged zeolite bed 102) with sulfur dioxide after removal of sulfolene (as described herein with respect to FIG. 4). In the particular embodiment illustrated in FIG. 5, at least a portion of the sulfur dioxide that is utilized for zeolite recharging is formed via thermal processing of the sulfolene that is scrubbed from the zeolite bed.

In the particular embodiment illustrated in FIG. 5, the first valve 110 is in the second operating position to direct the input stream 108 to the second $SO_2$-charged zeolite bed 104 (not shown in FIG. 5) for butadiene sequestration. FIG. 5 illustrates that the control device 116 may second a (second) valve positioning signal 502 to the second valve 130 to close the second fluid path to the first $SO_2$-charged zeolite bed 102. For example, the control device 116 may send the (second) valve positioning signal 502 to the second valve 130 after performing sulfolene removal operation(s), as described herein with respect to FIG. 4. Responsive to the (second) valve positioning signal 502, the second valve 130 may change from the second operating position (as shown in FIG. 4) to the first operating position (as shown in FIG. 5).

FIG. 5 further illustrates that the control device 116 may send a valve positioning signal 504 to the third valve 134, and the third valve 134 may change from the first operating position (as shown in FIG. 4) to a second operating position to allow for the zeolite recharging 136 with sulfur dioxide. For example, the control device 116 may send the valve positioning signal 504 to the third valve 134 after sending the (second) valve positioning signal 502 to the second valve 130. Thus, the first $SO_2$-charged zeolite bed 102 may be isolated from the sulfolene removal subsystem 120 (as shown in FIG. 4) in order to allow a second set of operations associated with zeolite recharging to be performed. While FIG. 5 illustrates a particular example in which sulfur dioxide that is formed from decomposition of sulfolene (as shown in FIG. 4) is recycled during the zeolite recharging 136, in other cases the sulfur dioxide that is used for the zeolite recharging 136 may represent "additional" sulfur dioxide that may be received from an alternative source.

While not shown in FIG. 5, after performing the second set of operations associated with the zeolite recharging 136, the control device 116 may send one or more additional valve positioning signals. As an example, the control device 116 may send an additional valve positioning signal to the third valve 134. Responsive to the additional valve positioning signal, the third valve 134 may change from the second operating position (as shown in FIG. 5) to the first operating position (as shown in FIG. 1). As another example, the control device 116 may send an additional valve positioning signal to the first valve 110. Responsive to the additional valve positioning signal, the first valve 110 may change from the second operating position (as shown in FIG. 5) to the first operating position (as shown in FIG. 1) in order to allow for butadiene sequestration at the first $SO_2$-charged zeolite bed 102. Alternatively, as described herein with respect to FIG. 3, the control device 116 may send the additional valve positioning signal to the first valve 110 after butadiene detected in the output stream 114 of the second $SO_2$-charged zeolite bed 104 exceeds the butadiene threshold. The second $SO_2$-charged zeolite bed 104 may then be scrubbed/recharged in a manner similar to that described above with respect to the first $SO_2$-charged zeolite bed 102.

Thus, FIG. 5 illustrates that, after removal of sulfolene that is formed as a result of a chemical reaction of sulfur dioxide and butadiene, a zeolite bed may be recharged with sulfur dioxide in order to allow the zeolite bed to be used for butadiene sequestration. In the example of FIG. 5, the sulfur dioxide that is used to recharge the zeolite bed is formed from thermal decomposition of the sulfolene that is removed from the zeolite bed. Alternatively, the zeolite bed may be recharged with sulfur dioxide from another source.

Figure 6:
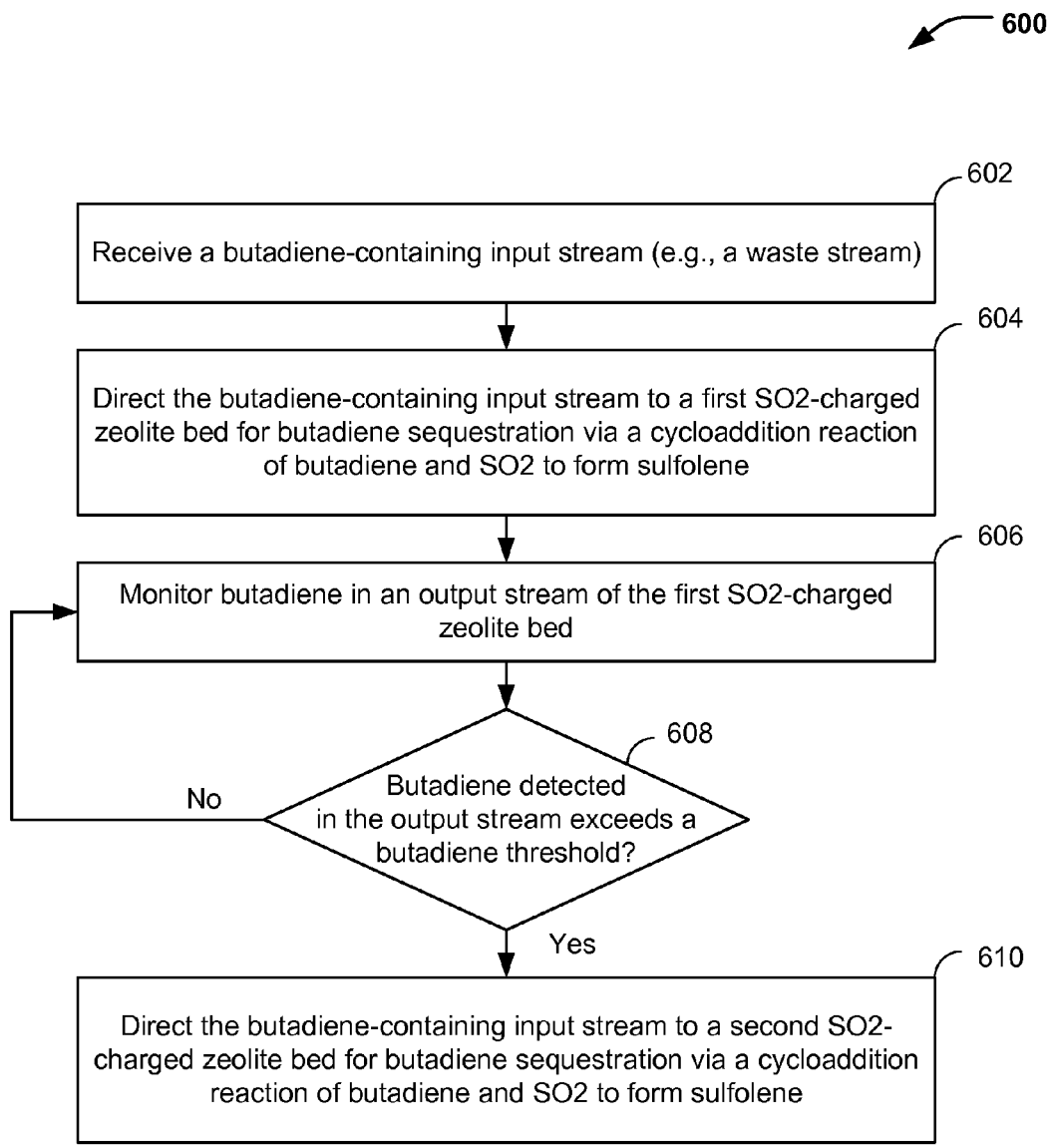
FIG. 6 is a flow diagram illustrating a particular embodiment of a method of removing butadiene from an input stream by directing the input stream to a sulfur dioxide charged zeolite bed for butadiene sequestration via a chemical reaction of butadiene and sulfur dioxide to form sulfolene.

FIG. 6 is a flow diagram that illustrates a particular embodiment of a method 600 of butadiene sequestration. In FIG. 6, an input stream (that includes butadiene) may be directed to a particular sulfur dioxide charged zeolite bed for butadiene sequestration via a chemical reaction of butadiene and sulfur dioxide to form sulfolene. FIG. 6 illustrates that butadiene may be monitored in an output stream (e.g., of a first sulfur dioxide charged zeolite bed). When butadiene detected in the output stream exceeds a butadiene threshold, a butadiene-containing input stream may be directed to another sulfur dioxide charged zeolite bed for butadiene sequestration.

The method 600 includes receiving a butadiene-containing input stream (e.g., a gaseous waste stream that includes butadiene), at 602. For example, referring to FIGS. 1 and 2, the input stream 108 that includes butadiene is received from the butadiene-containing gas source 106. In some cases, the input stream 108 may represent a gaseous waste stream. To illustrate, the butadiene may be produced during combustion or pyrolysis of organic compounds and/or through steam cracking of petroleum products.

The method 600 includes directing the butadiene-containing input stream to a first $SO_2$-charged zeolite bed for butadiene sequestration, at 604. Butadiene may be sequestered at the first $SO_2$-charged zeolite bed via a chemical reaction (e.g., a cycloaddition reaction) of butadiene and sulfur dioxide to form sulfolene. For example, referring to FIGS. 1 and 2, the input stream 108 that includes butadiene may be directed to the first $SO_2$-charged zeolite bed 102 for butadiene sequestration when the first valve 110 is in the first operating position. FIG. 2 further illustrates that butadiene may be sequestered (as solid sulfolene) at the first $SO_2$-charged zeolite bed 102 via a chemical reaction (e.g., a [4+1] cycloaddition reaction) of butadiene and sulfur dioxide to form sulfolene.

The method 600 includes monitoring butadiene in an output stream of the first $SO_2$-charged zeolite bed, at 606. For example, referring to FIGS. 1 and 2, the butadiene detector 112 may monitor butadiene in the output stream 114 of the first $SO_2$-charged zeolite bed 102.

The method 600 includes determining whether butadiene detected in the output stream of the first sulfur dioxide charged zeolite bed exceeds a butadiene threshold, at 608. For example, referring to FIGS. 1 and 2, the control device 116 may receive an indication from the butadiene detector 112 that butadiene detected in the output stream 114 exceeds a butadiene threshold. Butadiene exceeding the butadiene threshold may be indicative of inadequate sulfur dioxide being available at the first $SO_2$-charged zeolite bed 102 for chemical reaction with butadiene to form sulfolene.

When the butadiene threshold is not exceeded, the method 600 may return to 606, and butadiene may continue to be monitored in the output stream of the first sulfur dioxide charged zeolite bed. For example, referring to FIGS. 1 and 2, the butadiene detector 112 may continue to monitor the output stream 114 of the first $SO_2$-charged zeolite bed 102.

When the butadiene threshold is exceeded, the method 600 includes directing the butadiene-containing input stream to a second sulfur dioxide charged zeolite bed for butadiene sequestration, at 610. Butadiene may be sequestered at the second sulfur dioxide charged zeolite bed via a chemical reaction (e.g., a cycloaddition reaction) of butadiene and sulfur dioxide to form sulfolene. For example, referring to FIG. 3, the input stream 108 may be directed to the second $SO_2$-charged zeolite bed 104 when butadiene detected in the output stream 114 (of the first $SO_2$-charged zeolite bed 102 of FIGS. 1 and 2) exceeds the butadiene threshold. FIG. 3 further illustrates that the control device 116 may send the valve positioning signal 302 to the first valve 110 to change to the second operating position in order to provide a fluid path to the second $SO_2$-charged zeolite bed 104.

Thus, FIG. 6 illustrates that an input stream (that includes butadiene) may be directed to a particular $SO_2$-charged zeolite bed for butadiene sequestration via a chemical reaction of butadiene and sulfur dioxide to form sulfolene. An output stream of a $SO_2$-charged zeolite bed may be monitored for butadiene. When butadiene detected in the output stream exceeds a butadiene threshold that may be indicative of inadequate sulfur dioxide for reaction with butadiene, the input stream may be redirected to another $SO_2$-charged zeolite bed for butadiene sequestration. By monitoring butadiene in an output stream of a first $SO_2$-charged zeolite bed and selectively redirecting an input stream to a second $SO_2$-charged zeolite bed, the butadiene sequestration process may continue while the first zeolite bed is scrubbed and recharged.

Figure 7:
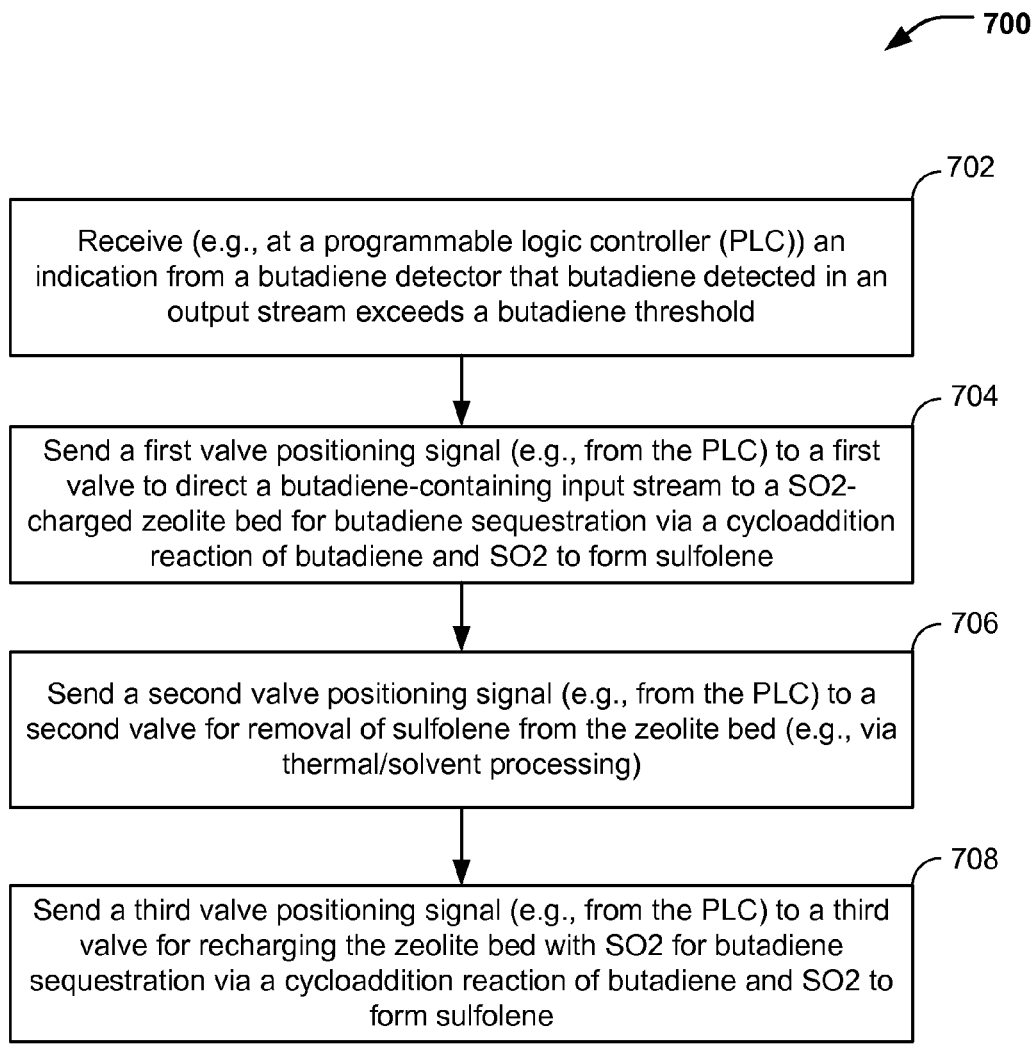
FIG. 7 is a flow diagram illustrating a particular embodiment of a method of controlling a process of butadiene sequestration.

FIG. 7 is a flow diagram that illustrates a particular embodiment of a method 700 of controlling a process of butadiene sequestration. In FIG. 7, a control device (e.g., a PLC device) may be utilized to send valve positioning signal(s) to direct an input stream that includes butadiene to a sulfur dioxide charged zeolite bed in response to butadiene detected in an output stream exceeding a butadiene threshold. FIG. 7 further illustrates that the control device may be utilized to send valve positioning signal(s) to allow for sulfolene removal from a zeolite bed and for sulfur dioxide recharging of the zeolite bed.

The method 700 includes receiving an indication from a butadiene detector that butadiene detected in an output stream exceeds a butadiene threshold, at 702. For example, referring to FIG. 3, the control device 116 may receive an indication from the butadiene detector 112 that butadiene detected in the output stream 114 (of the first $SO_2$-charged zeolite bed 102 shown in FIG. 2) exceeds a butadiene threshold.

The method 700 includes sending a first valve positioning signal to a first valve to direct a butadiene-containing input stream to a $SO_2$-charged zeolite bed for butadiene sequestration, at 704. Butadiene may be sequestered from the input stream via a chemical reaction (e.g., a cycloaddition reaction) of butadiene and sulfur dioxide to form sulfolene. For example, referring to FIG. 3, the control device 116 may send the valve positioning signal 302 to the first valve 110 to direct the input stream 108 that includes butadiene to the second $SO_2$-charged zeolite bed 104 for butadiene sequestration. FIG. 3 further illustrates that butadiene may be sequestered from the input stream 108 at the second $SO_2$-charged zeolite bed 104 via a chemical reaction of sulfur dioxide and butadiene to form (solid) sulfolene (e.g., at pore locations of the second $SO_2$-charged zeolite bed 104 that includes sulfur dioxide molecules that are hydrogen bonded to the zeolite bed).

The method 700 includes sending a second valve positioning signal to a second valve for removal of sulfolene from the zeolite bed (e.g., via thermal/solvent processing), at 706. For example, referring to FIG. 4, the control device 116 may send the valve positioning signal 402 to the second valve 130. Responsive to receiving the valve positioning signal 402, the second valve 130 may change to the second operating position to provide a (fluid) path for removal of sulfolene from the first $SO_2$-charged zeolite bed 102.

The method 700 includes sending a third valve positioning signal to a third valve for recharging the zeolite bed with sulfur dioxide, at 708. For example, referring to FIG. 5, after sending the (second) valve positioning signal 502 to the second valve 130, the control device 116 may send the valve positioning signal 504 to the third valve 134. Responsive to receiving the valve positioning signal 504, the third valve 134 may change to the second operating position to provide a fluid path for sulfur dioxide recharging.

Thus, FIG. 7 illustrates that a control device (e.g., a PLC device) may be used to control a butadiene sequestration process. For example, the control device may send valve positioning signals to different valves in order to prevent disruption of a butadiene sequestration process as a result of an inadequate supply of sulfur dioxide for reaction with butadiene at an $SO_2$-charged zeolite bed. FIG. 7 further illustrates that the control device may be used to send valve positioning signals to different valves in order to allow for sulfolene removal from a zeolite bed and for sulfur dioxide recharging of the zeolite bed (e.g., while an alternate $SO_2$-charged zeolite bed is being used for butadiene sequestration).

Figure 8:
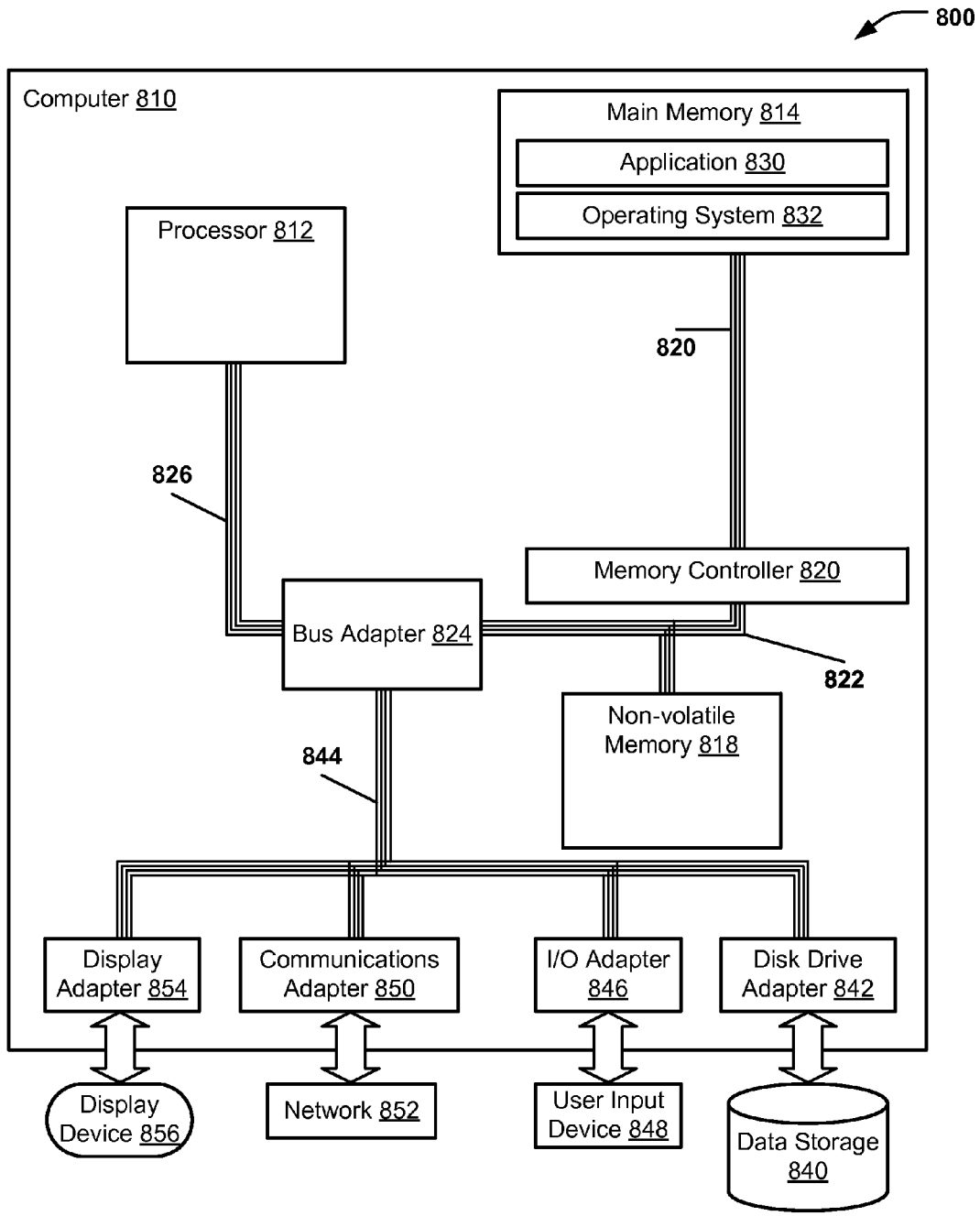
FIG. 8 is a block diagram of an exemplary computer system operable to support embodiments of computer-implemented methods, computer program products, and system components as illustrated in FIGS. 1-7.

Referring to FIG. 8, an exemplary automated computing machinery including a computer 810 is shown. The computer 810 is an exemplary implementation of the control device 116 illustrated and further described herein with respect to FIGS. 1-5. The computer 810 includes at least one computer processor (CPU) 812 as well as main memory 814, a memory controller 816, and a non-volatile memory 818. The main memory 814 is connected through a memory bus 820 to the memory controller 816. The memory controller 820 and the non-volatile memory 814 are connected through a memory bus 822 and a bus adapter 824 to the processor 812 through a processor bus 826.

Stored at the memory 814 is an application 830 that may be a module of user-level computer program instructions for carrying out particular tasks (e.g., the operations described with respect to controlling a butadiene sequestration process that utilizes a plurality of sulfur dioxide charged zeolite beds for butadiene sequestration). Also stored at the main memory 814 is an operating system 832. Operating systems include, but are not limited to, UNIX® (a registered trademark of The Open Group), Linux® (a registered trademark of Linus Torvalds), Windows® (a registered trademark of Microsoft Corporation, Redmond, Wash., United States), AIX® (a registered trademark of International Business Machines (IBM) Corp., Armonk, N.Y., United States) i5/OS® (a registered trademark of IBM Corp.), and others as will occur to those of skill in the art. The operating system 832 and the application 830 in the example of FIG. 8 are shown in the main memory 814, but components of the aforementioned software may also, or in addition, be stored at non-volatile memory (e.g., on data storage, such as illustrative data storage 840 and/or the non-volatile memory 818).

The computer 810 includes a disk drive adapter 842 coupled through an expansion bus 844 and the bus adapter 824 to the processor 812 and other components of the computer 810. The disk drive adapter 842 connects non-volatile data storage to the computer 810 in the form of the data storage 840 and may be implemented, for example, using Integrated Drive Electronics ("IDE") adapters, Small Computer System Interface ("SCSI") adapters, Serial Attached SCSI ("SAS") adapters, and others as will occur to those of skill in the art. Non-volatile computer memory also may be implemented as an optical disk drive, electrically erasable programmable read-only memory (so-called "EEPROM" or "Flash" memory), RAM drives, and other devices, as will occur to those of skill in the art.

The computer 810 also includes one or more input/output ("I/O") adapters 846 that implement user-oriented input/output through, for example, software drivers and computer hardware for controlling input and output to and from user input devices 848, such as keyboards and mice. In addition, the computer 810 includes a communications adapter 850 for data communications with a data communications network 852. In a particular embodiment, the communications adapter 852 may be utilized by the control device 116 of FIGS. 1-5 to communicate with the butadiene detector 112, the first valve 110, the second valve 130, or the third valve 134 to control a butadiene sequestration process. In some cases, the communications adapter 852 may be utilized by the control device 116 of FIGS. 1-5 to communicate with the sulfolene removal subsystem 120, the butadiene collection subsystem 122, the sulfur dioxide collection subsystem 124, or a combination thereof.

The data communications may be carried out serially through Recommended Standard 232 (RS-232) connections (sometimes referred to as "serial" connections), through external buses such as a Universal Serial Bus ("USB"), through data communications networks such as internet protocol (IP) data communications networks, and in other ways as will occur to those of skill in the art. The communications adapter 850 implements the hardware level of data communications through which one computer sends data communications to another computer, directly or through a data communications network. Examples of the communications adapter 850 suitable to use in the computer 810 include, but are not limited to, modems for wired dial-up communications, Ethernet (Institute of Electrical and Electronics Engineers (IEEE) 802.3) adapters for wired network communications, and IEEE 802.11 adapters for wireless network communications. The computer 810 also includes a display adapter 854 that facilitates data communication between the bus adapter 824 and a display device 856, enabling the application 830 to visually present output on the display device 856.

Particular embodiments described herein may take the form of an entirely hardware embodiment, an entirely software embodiment, or an embodiment containing both hardware and software elements. In a particular embodiment, the disclosed methods are implemented in software that is embedded in processor readable storage medium and executed by a processor that includes but is not limited to firmware, resident software, microcode, etc.

Further, embodiments of the present disclosure, may take the form of a computer program product accessible from a computer-usable or computer-readable storage medium providing program code for use by or in connection with a computer or any instruction execution system. For the purposes of this description, a computer-usable or computer-readable storage medium can be any apparatus that can tangibly embody a computer program and that can contain, store, communicate, propagate, or transport the program for use by or in connection with the instruction execution system, apparatus, or device.

In various embodiments, the medium can include an electronic, magnetic, optical, electromagnetic, infrared, or semiconductor system (or apparatus or device) or a propagation medium. Examples of a computer-readable storage medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and digital versatile disk (DVD).

A data processing system suitable for storing and/or executing program code may include at least one processor coupled directly or indirectly to memory elements through a system bus. The memory elements can include local memory employed during actual execution of the program code, bulk storage, and cache memories that may provide temporary or more permanent storage of at least some program code in order to reduce the number of times code must be retrieved from bulk storage during execution.

Input/output or I/O devices (including but not limited to keyboards, displays, pointing devices, etc.) can be coupled to the data processing system either directly or through intervening I/O controllers. Network adapters may also be coupled to the data processing system to enable the data processing system to become coupled to other data processing systems or remote printers or storage devices through intervening private or public networks. Modems, cable modems, and Ethernet cards are just a few of the currently available types of network adapters.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the scope of the disclosure. Thus, the present disclosure is not intended to be limited to the embodiments shown herein but is to be accorded the widest scope possible consistent with the principles and features as defined by the following claims.

The invention claimed is:

1. A butadiene sequestration system comprising:
   a first fluid interface to receive an input stream that includes butadiene;
   a first sulfur dioxide charged zeolite bed to sequester butadiene from the input stream via a chemical reaction of butadiene and sulfur dioxide to form sulfolene; and
   a second fluid interface to provide an output stream from the first sulfur dioxide charged zeolite bed.

2. The butadiene sequestration system of claim 1, further comprising a second sulfur dioxide charged zeolite bed to sequester butadiene from the input stream via a chemical reaction of the butadiene and sulfur dioxide to form sulfolene.

3. The butadiene sequestration system of claim 2, further comprising:
   a butadiene detector to monitor butadiene in the output stream;
   a control device communicatively coupled to the butadiene detector, wherein the control device is configured to send a valve positioning signal to a valve responsive to a determination that butadiene detected in the output stream exceeds a butadiene threshold, and wherein the valve is configured to direct the input stream to the second sulfur dioxide charged zeolite bed for butadiene sequestration responsive to receiving the valve positioning signal.

4. The butadiene sequestration system of claim 3, wherein the control device includes a programmable logic controller (PLC) device, and wherein the valve positioning signal includes instructions to close a first fluid path to the first sulfur dioxide charged zeolite bed and to open a second fluid path to the second sulfur dioxide charged zeolite bed.

5. The butadiene sequestration system of claim 1, further comprising:
   a second fluid interface for removal of the sulfolene from the first sulfur dioxide charged zeolite bed; and
   a third fluid interface for providing additional sulfur dioxide to the first sulfur dioxide charged zeolite bed for butadiene sequestration.

* * * * *